United States Patent [19]
Imura et al.

[11] Patent Number: 5,217,714
[45] Date of Patent: Jun. 8, 1993

[54] METHOD FOR STIMULATING THE SECRETION OF ACTH BY ADMINISTRATION OF IL-1B ANALOGUES

[75] Inventors: Hiroo Imura; Junichi Fukata, both of Kyoto; Yoshikatsu Hirai, Tokushima, all of Japan

[73] Assignee: Otsuka Pharmaceutical Co., Ltd., Tokyo, Japan

[21] Appl. No.: 409,193

[22] Filed: Sep. 19, 1989

[30] Foreign Application Priority Data

Sep. 19, 1988 [JP] Japan ............................. 63-234285

[51] Int. Cl.$^5$ ............................................. A61K 45/05
[52] U.S. Cl. .................................. 424/85.2; 530/351; 514/8; 514/12
[58] Field of Search ...................... 424/85.2; 530/351

[56] References Cited

FOREIGN PATENT DOCUMENTS 237967 9/1987 European Pat. Off. .

OTHER PUBLICATIONS

Naito et al. (1990) Biochem. Biophys. Res. Comm. 167(1):103–109.
Berkow (ed.), The Merck Manual of Diagnosis and Therapy, pp. 988–990, 1982.
Besedovsky, H. et al. (1986) Immunoregulatory Feedback Between Interleukin-1 and Glucocorticoid Hormones. Science 233:652–654.

*Primary Examiner*—Robert A. Wax
*Assistant Examiner*—Richard C. Ekstrom
*Attorney, Agent, or Firm*—Sughrue, Mion, Zinn, Macpeak & Seas

[57] ABSTRACT

A method for testing the inducibility of the hypothalamus to effect the secretion of andrenocorticotropic hormone comprising the steps of:

(a) administering to a test subject a pharmaceutically effective amount of a derivative of human IL-1$\beta$ selected from the group consisting of human IL-1$\beta$ [7-153], human IL-1$\beta$ [1-148], human IL-1$\beta$ [Gly$^4$], human IL-1$\beta$ [Leu$^{93}$] and human IL-1$\beta$ [des Arg$^{98}$]; and (b) measuring an increase in blood levels of at least one of adrenocorticotropic hormone, cortisol and corticotropin-releasing hormone, wherein the degree of increase in said blood levels of at least one of adrenocorticotropic hormone, cortisol and corticotropin-releasing hormone, corresponds to the degree of inducibility of the hypothalamus and is not substantially due to the induction of fever.

3 Claims, No Drawings

METHOD FOR STIMULATING THE SECRETION OF ACTH BY ADMINISTRATION OF IL-1B ANALOGUES

The present invention relates to drugs for testing the function of secreting adrenocorticotropic hormone (ACTH), and more particularly to a drug comprising a derivative of human interleukin 1β (IL-1β) for testing of the inducibility of the hypothalamus to effect the secretion of ACTH.

The steroid hormones secreted from the adrenal cortex serve important functions in maintaining the electrolyte balance and controlling saccharometabolism. ATCH, angiotensin II, artrial natriuretic polypeptide (ANP) and the like are known as factors acting on the adrenal cortex to alter the function of synthesizing glucocorticoids and the function of synthesizing mineralocorticoids. ACTH is one of the most important factors for synthesizing glucocorticoids in the adrenal cortex and regulating the secretion thereof. ACTH is one of the pituitary hormones whose synthesis is caused by the production of corticotropin-releasing hormone (CRH) secreted by the corticotroph cells in the hypothalamus. ACTH secretion is regulated with CRH produced by the hypothalamus.

Since the secretion of pituitary hormones is thus regulated by the hypothalamus, abnormalities in the secretion of anterior pituitary hormones include those attributable to the disorder of the hypothalamus and those attributable to the hypophysis itself. Besides secretion abnormalities due to organic lesions, presence of functional hormone secretion disorders is also known recently.

The methods of testing the function of secreting pituitary hormones are generally divided into two methods: one for use in the case where hypopituitarism is suspected, and the other for use in the case where hyperpituitarism is suspected. In the case of hyperpituitarism, hormone levels in blood measured only once are generally diagnostically valuable, and hyperpituitarism should be confirmed by conducting secretion inhibiting tests. However, in the case where hypopituitarism is suspected, pituitary hormone blood levels measured of the patient considerably overlap those in the normal person, so that the measurements are of low value. It is therefore generally necessary to conduct hormone secretion stimulating tests to check the hormone secreting function from the resulting reaction, and if hypopituitarism is substantiated, the site of disorder must be located through further examinations.

The secretion stimulating tests presently known for use in determining ACTH include those wherein CRH is used as a release stimulating factor which acts directly on the hypophysis, and those conducted via the hypothalamus, for example, with use of metyrapone (Metopirone), insulin or the like. Of these, the stimulating test via the hypothalamus is useful (1) as a screening test because it is adapted to check at a time when the function of the overall hormonal system including the hypothalamus, hypophysis and adrenal gland is in series, and also (2) as a stimulating test essential in establishing and diagonosing disorders in the hypothalamus itself. Nevertheless, of the test drugs presently in use, metyrapone possibly develops shock symptoms due to abrupt inhibition of adrenocortical hormone synthesis. Further, the hypoglycemia induction method by the intravenous administration of insulin produces a great stress, and therefore is not conducted for some patients, such as aged persons and those with coronary insufficiency.

Presently, endocrinological examinations have revealed that impaired secretion of ACTH leads to secondary adrenocortical insufficiency, lowers 17-OHCS in the urine and plasma cortisol, results in a delayed reaction against continuous ACTH load, and impairs the reaction of plasma ACTH or cortisol against insulin hypoglycemia and lysine-vasopressin (LVP) and the reaction of plasma ACTH, 11-deoxycortisol or 17-OHCS in the urine against metyrapone.

On the other hand, the present applicant has conducted intensive research on human IL-1β and derivatives thereof and found that some derivatives of human IL-1β have the ability to stimulate the secretion of pituitary hormones, especially ACTH, as entirely distinct from their original biological activity to activate the lymphocytes and increase the production of interleukin 2 (IL-2) and the production of antibodies, anti-inflammatory activity, activity to prevent radiation damage, etc., and that the stimulatory activity does not entail the inhibited synthesis of adrenocortical hormones to be induced by metyrapone or the hypoglycemia resulting from the administration of insulin. Accordingly, the applicant has found that the derivatives are useful for checking the patients with hypopituitarism or the like for the function of secreting pituitary hormones by stimulating the secretion of these hormones from an entirely novel viewpoint. These findings have matured to novel drugs and method for testing the hormone secreting function.

More specifically, the present invention provides a drug for testing of the inducibility of the hypothalamus to effect the secretion of ACTH. ACTH characterized in that the drug comprises an effective amount of a derivative of human IL-1β.

Thus, the drug of the present invention for testing the ACTH secreting function consists essentially of a derivative of human IL-1β as its active component. Such human IL-1β derivatives includes polypeptides have an amino acid sequence which corresponds to a modification of the 153-amino acid sequence of a polypeptide having LAF (lymphocyte activating factor) activity (native IL-1β, see Proc. Natl. Acad. Sci., Vo. 81, 7907-7911 (1984); Nature, Vol. 315, 641 (1985); Nucleic Acid Research, Vol. 13 (16) 5869 (1985); etc.)

The primary amino acid sequence of the native IL-1β is represented by the following formula.

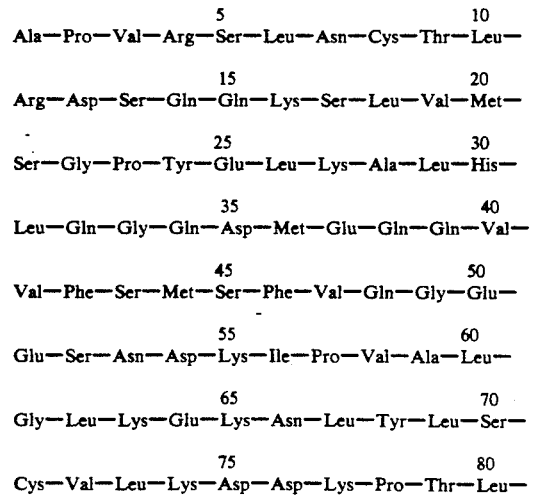

```
              5                    10
Ala—Pro—Val—Arg—Ser—Leu—Asn—Cys—Thr—Leu—

15                   20
Arg—Asp—Ser—Gln—Gln—Lys—Ser—Leu—Val—Met—

25                   30
Ser—Gly—Pro—Tyr—Glu—Leu—Lys—Ala—Leu—His—

35                   40
Leu—Gln—Gly—Gln—Asp—Met—Glu—Gln—Gln—Val—

45                   50
Val—Phe—Ser—Met—Ser—Phe—Val—Gln—Gly—Glu—

55                   60
Glu—Ser—Asn—Asp—Lys—Ile—Pro—Val—Ala—Leu—

65                   70
Gly—Leu—Lys—Glu—Lys—Asn—Leu—Tyr—Leu—Ser—

75                   80
Cys—Val—Leu—Lys—Asp—Asp—Lys—Pro—Thr—Leu—
```

-continued

```
              85                         90
Gln—Leu—Glu—Ser—Val—Asp—Pro—Lys—Asn—Tyr—

95                         100
Pro—Lys—Lys—Lys—Met—Glu—Lys—Arg—Phe—Val—

105                        110
Phe—Asn—Lys—Ile—Glu—Ile—Asn—Asn—Lys—Leu—

115                        120
Glu—Phe—Glu—Ser—Ala—Gln—Phe—Pro—Asn—Trp—

125                        130
Tyr—Ile—Ser—Thr—Ser—Gln—Ala—Glu—Asn—Met—

135                        140
Pro—Val—Phe—Leu—Gly—Gly—Thr—Lys—Gly—Gly—

145                        150
Gln—Asp—Ile—Thr—Asp—Phe—Thr—Met—Gln—Phe—

Val—Ser—Ser
```

Typical of the IL-1β derivatives are those disclosed in a preceding application filed by the present applicant (see Unexamined Japanese Patent Publication SHO 63-152398 (Laid-Open EP Application No.0237967)). Among these, especially preferable are as follows.

Human IL-1β [7-153]: human IL-1β derivative having an amino acid sequence corresponding to that of native IL-1β wherein the amino acids at the 1- to 6- positions are deficient.

Human IL-1β [1-148]: human IL-1β derivative having an amino acid sequence corresponding to that of native IL-1β wherein the amino acids at the 149- to 153-positions are deficient.

Human IL-1β [Gly$^4$]: human IL-1β derivative corresponding to native human IL-1β wherein the amino acid (Arg) at the 4-position is replaced by Gly.

Human IL-1β [Leu$^{93}$]: human IL-1β derivative corresponding to native human IL-1β wherein the amino acid (Lys) at the 93-position is replaced by Leu.

Human IL-1β [des Arg$^{98}$]: human IL-1β derivative corresponding to native human IL-1β wherein the amino acid (Arg) at the 98-position is deficient.

These human IL-1β derivatives can be prepared and isolated by known gene engineering techniques. Specific procedures therefor, etc. are disclosed in the above-mentioned patent publication.

The test drug of the present invention comprises the human IL-1β derivative as its active component, and the other components thereof can be the same as those used for common test drugs of this type. Usually the derivative is used along with desired additives such as those generally used pharmaceutically and is formulated into a drug for actual use as diluted with a suitable diluent. Examples of useful additives are those contributing to the stabilization of human IL-1β, such as human serum albumin (HSA) and like albumins, cysteine, glycine and like L-amino acids, etc. Also usable are glucose, mannitol, inositol, sucrose, maltose, dextran and like saccharides, ionic or nonionic surfactants, etc. The diluent to be used is usually distilled water for injections, which may contain buffers to give an adjusted pH of 4 to 8. Examples of useful buffers are citric acid-sodium phosphate, citric acid-sodium citrate, acetic acid-sodium acetate, disodium hydrophosphate-sodium dihydrophosphate, citric acid-boric acid and the like.

The test drug of the invention thus obtained and containing the human IL-1β derivative is administered through a suitable route in accordance with the type of pharmaceutical preparation thereof. For example when in the form of an injectable composition, the drug is given intravenously, intramuscularly, subcutaneously, intracutaneously or intraperitoneally. The amount of active component in the preparation, as well as the dosage of the preparation, is suitably determined according to the method, form and purpose of administration, the patient to be given the drug, etc. and is variable. Usually, however, it is desirable that the preparation contain about 0.00001 to 80 w/v % of the active component and be administered at a daily dose of about 0.01 μg to about 10 mg, calculated as the active component, for the adult. The preparation need not always be given only once a day but can be given dividedly three to four times a day.

The method of testing the ACTH secreting function with use of the present drug can be practiced in the same manner as the conventional hypophysis stimulating test, more specifically in the following manner. First, one of human IL-1β [7-153], human IL-1β [1-148], human IL-1β [Gly$^4$], human IL-1β [Leu$^{93}$] and human IL-1β[des Arg$^{98}$] in the form of a preparation formulated as above to serve as the test drug is administered usually intravenously at a dose of about 0.01 μg to about 10 mg. The blood is collected before the administration and also during a period of 120 minutes or 240 minutes following the administration at time intervals. The plasma or serum is separated off by the usual method from each blood preparation collected to prepare a test sample, and the concentration of ACTH, cortisol (adrenocortical glucocorticoid hormone) or CRH in the sample is determined by usual radioimmunoassay.

The variations in the hormone concentration of the blood thus determined are compared with those in the normal person, whereby the function of secreting the hormone can be tested. In this way, the test drug can be used for diagnosing panhypopituitarism, Sheehan's syndrome, Addison disease, ACTH deficiency, steroid withdrawal syndrome, anorexia nervosa, hypothalamic syndrome, Cushing's syndrome, etc.

The test method with use of the drug of the invention has the following advantages.

1) Malfunctions in the hypothalmus-hypophysis-adrenal cortex system can be diagnosed by a single testing procedure.
2) Lesions in the hypothalamus can be established and diagnosed when the present test method is practiced in combination with other test methods.
3) The method is almost unlikely to entail undesirable side effects. When administered to the living body, the human IL-1β derivative for use in the invention raises ACTH blood levels without inducing fever.
4) Since the present drug acts through a different mechanism from those used in conventional hypothalamus stimulating methods, the present method detects malfunctions from a novel viewpoint.
5) The test drug is analogous to a substance which is originally present in the human body and is less likely to cause foreign reactions.

As described above, the present invention has established a convenient and safe method of testing the pituitary function, thus providing a method of diagnosing hypopituitarism.

The present invention will be described in greater detail with reference to the following examples.

EXAMPLE 1

Preparation of Drug for Testing ACTH Secreting Function

To a solution of IL-1β [7-153] in physiological saline ($1 \times 10^6$ units/ml in terms of GIF activity) was added human serum albumin (HSA) to a concentration of 0.5%, the mixture was filtered (using 0.22-μm membrane filter), asceptically placed into vials dividedly in an amount of 1 ml in each vial and lyophilize to obtain an injectable preparation.

The preparation thus obtained is diluted with 1 ml of distilled water for injection when to be used.

EXAMPLE 2

Pharmacological Efficacy Test I

The test drug of the invention was used for testing the ACTH secreting function.

Given below are the derivatives of human IL-1β used as active components in this test. These derivatives are all disclosed in the aforementioned patent publication.

Human IL-1β [7-153]: human IL-1β derivative having an amino acid sequence corresponding to that of native IL-1β wherein the amino acids at the 1- to 6- positions are deficient.

Human IL-1β [1-148]: human IL-1β derivative having an amino acid sequence corresponding to that of native IL-1β wherein the amino acids at the 149- to 153-positions are deficient.

Human IL-1β Gly$^4$]: human IL-1β derivative corresponding to native human IL-1β wherein the amino acid (Arg) at the 4-position is replaced by Gly.

Human IL-1β Leu$^{93}$]: human IL-1β derivative corresponding to native human IL-1β wherein the amino acid (Lys) at the 93-position is replaced by Leu.

Human IL-1β [des Arg$^{98}$]: human IL-1β derivative corresponding to native human IL-1β wherein the amino acid (Arg) at the 98-position is deficient.

These derivatives were used as diluted to a specified concentration with saline for injection use containing 100 μg/ml of bovine serum albumin (product of Otsuka Pharmaceutical Factory, Inc.).

Wistar male rats (weighing 300 to 350 g) were used. A catheter was inserted into the right atrium of each animal as anesthetized with pentobarbital. An administration experiment was conducted after a recovery period of at least 24 hours, using special cages designed to minimize nonspecific stress. The rats were held in the cages overnight before the experiment (Fukata J. et al., Neuroendocrinology, 40, 193-200 (1985)).

On the day of experiment, the rats were divided into groups, five in each group, the blood was collected before the administration, IL-1β derivative was intravenously given without anesthetization and free of restraint. The blood was collected four times, 15 minutes, 30 minutes, 60 minutes and 120 minutes after the administration, in an amount of 0.6 ml each time.

A small quantity of heparin was added to each blood sample collected, the plasma was then separated off at 4° C., and the blood cells were suspended in saline in the same amount as the plasma collected and were intravenously returned to the animal after the subsequent blood collection.

The concentration of ACTH in the blood was determined after extraction by the silicic acid method (Nakao, K et al., J. Clin. Invest., 62, 1395-1398 (1978)), using anti-ACTH anti-serum (West) provided by NIAMDD National Pituitary Agency.

The ACTH extraction ratio in the system was 80%, sensitivity was 30 pg/ml, and interassay and intraassay C.V were each up to 10%.

The results were statistically processed by analysis of variance. The level of significance was 5%, hence significant.

Table 1 shows the variations in the concentration of ACTH in the blood with the lapse of time, in terms of m±SE, pg/ml.

TABLE 1

| Test group | Control | After 15 min | After 30 min |
|---|---|---|---|
| IL-1β [7-153] | 68 ± 10 | 210 ± 29 | 201 ± 27 |
| IL-1β [1-148] | 88 ± 12 | 258 ± 29 | 194 ± 18 |
| IL-1β [Gly$^4$] | 53 ± 4 | 310 ± 27 | 342 ± 24 |
| IL-1β [Leu$^{93}$] | 80 ± 18 | 321 ± 17 | 255 ± 17 |
| IL-1β [des Arg$^{98}$] | 117 ± 5 | 221 ± 26 | 213 ± 33 |

| Test group | After 60 min | After 120 min |
|---|---|---|
| IL-1β [7-153] | 158 ± 19 | 107 ± 22 |
| IL-1β [1-148] | 121 ± 24 | 80 ± 13 |
| IL-1β [Gly$^4$] | 250 ± 14 | 126 ± 15 |
| IL-1β [Leu$^{93}$] | 180 ± 19 | 96 ± 12 |
| IL-1β [des Arg$^{98}$] | 154 ± 16 | 117 ± 4 |

As will be apparent from the above table, the ACTH blood level increased to a maximum within 15 to 30 minutes after the administration of the human IL-1β derivative in each of the test groups, hence a significant increase in the ACTH blood level. On the other hand, no variation occurred in the ACTH blood level in each control group to which was given only the saline containing 100 μg/ml of bovine serum albumin and used as a solvent for the derivative.

No significant differences were found between the test groups in levels before the administration and in maximum levels after the administration.

EXAMPLE 3

Pharmacological Efficacy Test II

The human IL-1β derivatives used in the test I were checked for GIF activity (50% max. U/mg) and LAF activity (50% max. U/mg) and also for fever inducing activity.

The GIF activity and LAF activity were determined by the following methods.
1) Determination of GIF activity Portions (0.1 ml) of the test solution diluted to varying concentrations were placed into the wells of 96-well microplate (Corning Co., Ltd.), 0.1 ml of Eagle's MEM suspension containing 10% FCS containing human melonoma cells A375 in an amount of $2 \times 10^4$ cells/ml was then placed into each well, and the cells were incubated in a $CO_2$ incubator (Napco Co., Ltd.) for 4 days. After the incubation, 0.05 ml of 0.05% Neutral Red (Wako Junyaku Co., Ltd.) was placed into each well, followed by incubation at 37° C. for 2 hours. After removing the supernatant, 0.3 ml of phosphoric acid buffer saline was gently poured into each well for washing. After removing the washing, 0.1 ml of a mixture of sodium phosphate monobasic and ethanol in equal amounts was placed into each well, the plate was shaken for several minutes by a micromixer, and the amount of pigment taken into the cell was measured at an absorbance of 540 mμ using a photometer for 96-well microtitration plates (Titer check multiscane, Flow Lab.) to determine growth inhibition activity. The test group exhibiting 50% of the inhibition of cell growth of the control group, i.e., the test group which exhibited ½ the absorbance measured of the control group, was identified. The reciprocal of the number of times of dilution for the test group was taken as the GIF activity unit. Accordingly, when the GIF activity is 10 units, for example, the test solution, if diluted tenfold, still has activity to inhibit cell growth 50%.

(2) Determination of LAF activity

LAF activity was determined according to the method of J. J. Oppenheim et al. (J. Immunol., 116, 1466 (1976)) using thymocytes of C3H/He J strain mice.

For the determination of activity to induce fever, a specified quantity of the derivative was dissolved in PBS(-) containing 200 μg/ml of rat serum albumin, the solution was subcutaneously given to SD rats (male, 160 to 220 g), and the body temperature of each rat was measured at a time interval. The fever inducing activity was evaluated from the value 6 hours after the administration when the temperature rose to a maximum level, according to the following criteria.

| | |
|---|---|
| − | $0 \leq \Delta °C. < 1$ |
| + | $1 \leq \Delta °C. < 2$ |
| ++ | $2 \leq \Delta °C. < 3$ |

Table shows the results.

TABLE 2

| Test group | GIF activity | LAF activity |
|---|---|---|
| IL-1β [7-153] | $2.6 \times 10^4$ | $4 \times 10^3$ |
| IL-1β [1-148] | $9.9 \times 10^4$ | $2 \times 10^4$ |
| IL-1β [Gly$^4$] | $5.0 \times 10^6$ | $3 \times 10^5$ |
| IL-1β [Leu$^{93}$] | $3.3 \times 10^3$ | $8 \times 10^4$ |
| IL-1β [des Arg$^{98}$] | $1.4 \times 10^3$ | $1 \times 10^3$ |

| | Fever inducting activity | | | | |
|---|---|---|---|---|---|
| Amount given (μg/kg) | 0.001 | 0.1 | 1 | 10 | 100 |
| IL-1β [7-153] | − | − | − | − | + |
| IL-1β [1-148] | − | − | − | − | − |
| IL-1β [Gly$^4$] | − | − | − | + | ++ |
| IL-1β [Leu$^{93}$] | − | − | − | − | ++ |
| IL-1β [des Arg$^{98}$] | − | − | − | − | − |
| Native IL-1β | − | + | + | ++ | ++ |

Table 2 and the preceding Table 1 reveal the following. The derivative of human IL-1β for use as the active component of the test drug of the invention is very low in fever inducing activity (1/1000 to 1/10000 of that of native human IL-1β (see Table 2), but has high ability to stimulate the secretion of ACTH (see Table 1). This appears to indicate that the activity of the IL-1β derivative on the hypophysis to stimulate the production and secretion of CRH and ACTH originates in a site different from the fever inducing site on the IL-1 molecule. Manifestly, therefore, the derivative of human IL-1β is usable conveniently and with safety for testing and activating the function of the hypophysis.

We claim:

1. A method for testing the inducibility of the hypothalamus to effect the secretion of adrenocorticotropic hormone comprising the steps of:
   a) administering to a test subject a pharmaceutically effective amount of a derivative of human IL-1β selected from the group consisting of human IL-1β [7-153], human IL-1β [1-148], human IL-1β [Gly$^4$], human IL-1β [Leu$^{93}$] and human IL-1β [des Arg$^{98}$]; and
   (b) measuring an increase in blood levels of at least one of adrenocorticotropic hormone, cortisol and corticotropin-releasing hormone, wherein the degree of increase in said blood levels of at least one of adrenocorticotropic hormone, cortisol and corticotropin-releasing hormone, corresponds to the degree of inducibility of the hypothalamus and is not substantially due to the induction of fever.

2. A method according to claim 1, wherein said pharmaceutically effective amount is in the range of 0.01 μg to 10 mg.

3. A method according to claim 2, wherein said method is used to diagnose a disease selected from the group consisting of panhypopituitarism, Sheehan's syndrome, Addison's disease, adrenocorticotropic hormone deficiency, steroid withdrawal syndrome, anorexia nervosa, hypothalamic syndrome and Cushing's syndrome.

* * * * *